United States Patent
Maloh et al.

(10) Patent No.: US 12,194,068 B2
(45) Date of Patent: Jan. 14, 2025

(54) DIETARY SUPPLEMENT COMPOSITION FOR TREATING AND MANAGING ACNE

(71) Applicant: CODEX LABS CORPORATION, San Jose, CA (US)

(72) Inventors: Jessica Maloh, Toronto (CA); Barbara A. Paldus, San Jose, CA (US); Raja Sivamani, Sacramento, CA (US)

(73) Assignee: CODEX LABS CORPORATION, San Jose, CA (US)

(*) Notice: Subject to any disclaimer, the term of this patent is extended or adjusted under 35 U.S.C. 154(b) by 0 days.

(21) Appl. No.: 18/633,805

(22) Filed: Apr. 12, 2024

(65) Prior Publication Data

US 2024/0277789 A1 Aug. 22, 2024

Related U.S. Application Data

(63) Continuation of application No. 18/443,762, filed on Feb. 16, 2024.

(60) Provisional application No. 63/485,346, filed on Feb. 16, 2023.

(51) Int. Cl.
| | |
|---|---|
| A61K 35/747 | (2015.01) |
| A61K 9/00 | (2006.01) |
| A61K 31/353 | (2006.01) |
| A61K 31/57 | (2006.01) |
| A61K 35/00 | (2006.01) |
| A61K 35/742 | (2015.01) |
| A61K 35/745 | (2015.01) |
| A61K 36/328 | (2006.01) |
| A61K 36/82 | (2006.01) |
| A61K 45/06 | (2006.01) |
| A61P 17/10 | (2006.01) |

(52) U.S. Cl.
CPC .......... *A61K 35/747* (2013.01); *A61K 9/0053* (2013.01); *A61K 31/353* (2013.01); *A61K 31/57* (2013.01); *A61K 35/742* (2013.01); *A61K 35/745* (2013.01); *A61K 36/328* (2013.01); *A61K 36/82* (2013.01); *A61K 45/06* (2013.01); *A61P 17/10* (2018.01); *A61K 2035/115* (2013.01)

(58) Field of Classification Search
CPC .... A61K 31/715; A61K 35/747; A61K 31/10; A61K 31/198; A61K 31/202; A61K 31/593; A61K 31/7008; A61K 31/702; A61K 31/732; A61K 33/30; A61K 35/741; A61K 35/742; A61K 35/744; A61K 35/745; A61K 36/00; A61K 45/06; A61P 1/00

See application file for complete search history.

(56) References Cited

U.S. PATENT DOCUMENTS

| | | | |
|---|---|---|---|
| 5,079,164 A | 1/1992 | Kirkovits | |
| 2013/0316017 A1* | 11/2013 | Hynes | A61K 36/38 424/769 |
| 2019/0282637 A1* | 9/2019 | Simon | A61K 33/30 |

OTHER PUBLICATIONS

Brockway, "Probiotics in dermatology: acne as a case study," The Secret Life of Skin, available Aug. 24, 2022, accessed via: https://thesecretlifeofskin.com/2022/08/24/acne-probiotics/.
Chilicka et al,. "Microbiome and Probiotics in Ance Vulgaris—A Narrative Review," Life 12:422 (2022).
Fabbrocini et al., "Supplementation with Lactobacillus rhamnosus SP1 normalises skin expression of genes implicated in insulin signalling and improves adult acne," Beneficial Microbes 7:625-630 (2016).
Gueniche et al., "Randomised double-blind placebo-controlled study of the effect of *Lactobacillus paracasei* NCC 2461 on skin reactivity," Beneficial Microbes 5(2):137-145 (2014).
Jung et al., "Prospective, randomized, open-label trial comparing the safety, efficacy, and tolerability of an acne treatment regimen with and without a probiotic supplement and minocycline in subjects with mild to moderate acne," J Cutan Med Surg. 17(2): 114-22 (2013).
Kim et al., "*Lactobacillus acidophilus* suppresses intestinal inflammation by inhibiting endoplasmic reticulum stress," J Gastroenterol Hepatol. 34(1):178-185 (2019).
Kober and Bowe, "The effect of probiotics on immune regulation, acne, and photoaging," Int J Womens Dermatol. 1(2):85-89 (2015).
Lu and Hsu, "Does supplementation with green tea extract improve acne in post-adolescent women? A randomized, double-blind, and placebo-controlled clinical trial," Complement Ther Med. 25:159-163 (2016).
Philippe et al., "*Bifidobacterium lactis* attenuates onset of inflammation in a murine model of colitis," World J Gastroenterology 17(4): 459-469 (2011).
Priya et al., "The role of guggulsterone on the NF-$_K$B pathway in inflammatory bowel disease: preclinical evidence," Future Sci. OA 8(6): FSO803.
Rastogi and Singh, "Gut microbiome and human health: Exploring how the probiotic genus *Lactobacillus* modulate immune responses," Front Pharmacol 13:1042189 (2022).
Rinaldi et al., "Facial Acne: A Randomized, Double-Blind, Placebo-Controlled Study on the Clinical Efficacy of a Symbiotic Dietary Supplement," Dermatol Ther. 12(2):577-589 (2022).
Rybak et al., "Prospective Placebo-Controlled Assessment of Spore-Based Probiotic Supplementation on Sebum Production, Skin Barrier Function, and Acne," J Clin Med. 12(3):895 (2023).
Thappa and Dogra, "Nodulocystic Acne: Oral Gugulipid versus Tetracycline," J Dermatol 21:729-731 (1994).

* cited by examiner

Primary Examiner — Jana A Hines
(74) Attorney, Agent, or Firm — MEDLER FERRO WOODHOUSE & MILLS PLLC

(57) ABSTRACT

The present disclosure relates to compositions and methods useful for dietary augmentation to provide therapeutic intervention for the treatment and management of acne-prone skin. According to one embodiment of the present disclosure, there is provided an orally administrable composition containing a therapeutically effective amount of: (a) a probiotic blend of bacterial components containing at least: (i) *Lactobacillus acidophilus*, (ii) *Bifidobacterium lactis*, an (iii) *Bacillus coagulans*; (b) guggul; and (c) green tea leaf.

15 Claims, No Drawings

DIETARY SUPPLEMENT COMPOSITION FOR TREATING AND MANAGING ACNE

FIELD OF THE INVENTION

The present disclosure relates to orally administered supplement compositions and methods of treating, ameliorating, and managing acne. Supplement compositions are provided comprising a blend of probiotic microorganisms in combination with certain plant-derived actives that provide a synergistic acne treatment effect.

BACKGROUND

Acne vulgaris (acne) is a multifactorial disease that manifests in areas rich in sebaceous glands such as the face, and the trunk. It is one of the most common dermatoses affecting both men and women. Among its most common forms are comedonal acne, commonly known as juvenile acne, papulopustular and/or nodular acne, acne conglobate and "exogenous" acne which appears in response to external inflammatory factors. More particularly, acne is a disease of the pilosebaceous gland. The acne lesions can be inflammatory (papules and pustules) and/or non-inflammatory (open and closed comedones). The following four pathogenic factors play a determining role in the formation of acne: overproduction of sebum (seborrhea), irregular desquamation, bacterial colonization, and inflammation.

In the deepest parts of the infundibular portion of the hair follicle, there is the formation of a higher number of keratinocytes than normal. These cells differentiate into the cells of the stratum corneum that gradually block the lumen of the follicular canal. The physiological process of continuous desquamation of the acro-infundibulum to the surface is disturbed by the increased adhesion of the horny cells produced. It forms a hyperkeratotic plug called a comedone, the initial lesion of acne. Finally, the three predominant local bacteria, Staphyloccus epidermidis, Malassezia furfur and Cutibacterium acnes, are found in the sebaceous follicle and multiply as a result of the plugged environment. The alteration of the sebum medium and the improvement of microflora growth conditions lead to an increase in pro-inflammatory products such as lipases, proteases, and interleukins. It is assumed that the lipases produced dissociate triglycerides into free fatty acids, which then act as irritants for the follicular epithelium and thereby stimulate hyperproliferation. As the inflammatory process intensifies, granulocytes are attracted and migrate into the follicle lumen where they ultimately contribute to enzymatic disruption of the follicular wall.

Recent studies have also begun to explore the relationship between the body's microbiome and acne. It is increasingly believed that the interaction between skin microbes and host immunity plays an important role in this disease, with perturbed microbial composition and activity found in acne patients. Cutibacterium acnes (C. acnes; formerly called Propionibacterium acnes) is commonly found in sebum-rich areas and its over-proliferation has long been thought to contribute to the disease. However, information provided by advanced metagenomic sequencing has indicated that the cutaneous microbiota in acne patients and acne-free individuals differ at the virulent-specific lineage level. Acne also has close connections with the gastrointestinal tract, and many argue that the gut microbiota could be involved in the pathogenic and/or inflammatory processes of acne. The emotions of stress (e.g., depression and anxiety), for instance, have been hypothesized to aggravate acne by altering the gut microbiota and increasing intestinal permeability, potentially contributing to skin inflammation. Over the years, an expanding body of research has highlighted the existence of a gut-skin axis that connects gut microbes, oral probiotics, and diet, to acne severity.

The gut microbiome has several functions, including gathering of indigestible food particles and assimilating of nutrients such as vitamins, short-chain fatty acids, and minerals, while working in synergy with the liver to detoxify and eliminate toxic foreign compounds that may be present in the environment. Millions of microbial genes have been identified in the gut that support essential and necessary human functions. The gut is the primary site of intricate interactions between genes and the extrinsic immunological influence on the body, making it one of the most important organs for communicating with the environment. Bacteria that enter through the gut wall and into the bloodstream can cause systemic inflammation in the absence of a healthy intestinal wall. The gut wall, on the other hand, is protected by a variety of chemical and physical innate defense mechanisms that function in tandem with a local adaptive immune system. Many skin conditions have been linked to gastrointestinal inflammation, including rosacea, psoriasis, and acne.

Stress and depression can increase the permeability of the intestinal barrier. The result is a "leaky gut", which allows bacteria to infiltrate the circulation, triggering an inflammatory response. Indeed, both depression and stress can lead to increased inflammation and permeability of the gut. If the stress response is triggered too often, the body finds it harder to recover. This hampers digestion and can lead to stomach upsets. It can also contribute to the development of irritable bowel syndrome and/or ulcers. The digestive system cannot function properly if it is over-stressed or over-stimulated. This chronic inflammation can then weaken the skin barrier, degrade collagen and impair overall immunity. Long-term high stress can also aggravate existing skin problems. For example, stress can aggravate psoriasis, rosacea and eczema. It can also cause hives and other types of rash and trigger a flare-up of fever blisters. Although it's unlikely that poor gut health is the sole cause of acne development, digestive problems are more common in acne sufferers than in those without. Interestingly, around 70% of the body's immune cells reside in the gut, where they are influenced by the intestinal microbiome.

Skin and gut tissue have much in common. Although their primary roles are different, together they serve to protect the body from the outside world. Their respective epithelial cells have receptors which learn to react to specific microbes, environmental agents, and physical damage. They are rich in blood vessels and nerves, and both play crucial immune and neuroendocrine roles. Our skin and gut are in a constant struggle, fighting to maintain homeostasis with their microbiota, and these tissues use similar tactics to keep their microbiota in check such as frequently shedding their outer cells, secreting protective fluids with powerful bioactive substances, and closely working with the immune system to modulate inflammation. Because of their common embryonic origin, it is unsurprising that gut and skin epithelial cells will respond to many of the same biologically active molecules, although not necessarily in the same way or to the same extent. With both tissues connected by circulating blood, it is easy to see the role they play in the gut-skin axis.

Gut dysbiosis can lead to inflammation and the release of inflammatory messengers called cytokines, which can contribute to the development of acne. This inflammation can also damage the lining of the gut, allowing bacterial byproducts to pass from the gut through the bloodstream to the skin, where they can affect skin health locally, promoting the growth of acne-triggering bacteria.

On the other hand, more harmful microbes can trigger an immune response, increasing inflammation both in the gut and potentially elsewhere in the body. For example, enterobacteria, a large class of facultative gram-negative bacteria, are generally associated with many inflammatory diseases such as IBD (chronic inflammatory bowel disease) and obesity.

While the importance of a balanced, optimally diverse gut microbiome to one's overall health is clear, changes in the abundance or diversity of members of the gut microbiome can be associated with skin disease. Specific metabolic byproducts of gut microbes can directly influence normal physiology and disease processes. Factors that influence the diversity and composition of the gut microbial community can be grouped into three categories: non-host factors (such as environmental determinants), host factors (such as pancreatic enzymes, bile acids, pH), and bacterial factors (such as microbial enzymes, adhesive ability). Gut dysbiosis, which can be thought of as an imbalance in the composition and abundance of gut bacteria can negatively impact skin health. Biomarkers such as free phenol, p-cresol, and aromatic amino acid derivatives are thought to be produced by a disturbed gut. Conversely, a lack of production of sufficient quantities of short-chain fatty acid such as butyrate, caused by gut dysbiosis, is believed to lead to dysfunction of the skin barrier and skin inflammation. Dysbiosis in the gut contributes to three common skin disorders: psoriasis, atopic dermatitis, and acne. There are also reports on the association of gut dysbiosis with some less common but chronic skin diseases, such as rosacea, alopecia areata, hidradenitis suppurativa, erythema nodosum, and pyoderma gangrenosum. Furthermore, epidemiological studies and clinical trials suggest that modulation of the gut microbiome may influence susceptibility to allergic diseases and asthma.

Several studies have indicated a correlation between gut dysbiosis and acne vulgaris. A recent study revealed a significant reduction in the prevalence of Actinobacteria, *Bifidobacterium, Butyricicoccus, Coprobacillus*, and *Lactobacillus* species along with an increased abundance of Proteobacteria in persons with acne vulgaris. Further, it has been found that the gut microbiota of acne sufferers is reported to be of a higher ratio of Bacteroidetes to Firmicutes and is overall less diverse. It has been hypothesized that sterol regulatory element-binding protein 1 (SREBP-1), sebum fatty acid, and sebum triglyceride become stimulated by nutrient signaling disruption and lead to overgrowth of *Cutibacterium acnes*. In addition to the gut microbiome, various metabolic pathways also influence the pathophysiology of acne vulgaris, such as the mTOR pathway, which is activated by high glycemic load. The high glycemic load is the sole contributor to increased insulin/insulin-like growth factor (IGF-1) signaling, enhancing the cytoplasmic expression of FOXO1 (Forkhead box transcription factor 01). FOXO1 then stimulates the mammalian target of rapamycin complex 1 (mTORC1), which ultimately leads to acne development.

To date, there have been few studies comparing the gut microbiota of people with and without acne. Those that have been published, however, do suggest that there are in fact significant differences in the gut microbiota of acne sufferers. In view of the gut-skin axis being a two-way conversation facilitated by a continually learning host immune system, cytokines associated with acneic skin may be preventing the gut microbiota from naturally rebalancing. Probiotics could therefore be the key to re-establishing a healthy gut microbiota, even during severe and long-standing acne breakouts.

Among the probiotic strains of live microorganisms that are proving to be effective for acne is a blend of *Bifidobacterium breve, Lacticaseibacillus casei*, and *Ligilactobacillus salivarius*. In a randomized, double-blind clinical study, involving 114 subjects with mild to moderate acne, a 40% reduction in superficial inflammatory lesions was observed after 8 weeks in those taking the blend compared to the placebo group who experienced only a 10% reduction. Sec, Rinaldi F, Marotta L, Mascolo A, Amoruso A, Pane M, Giuliani G, Pinto D. Facial Acne: A Randomized, Double-Blind, Placebo-Controlled Study on the Clinical Efficacy of a Symbiotic Dietary Supplement. Dermatol Ther (Heidelb). 2022 February; 12(2):577-589. doi: 10.1007/s13555-021-00664-z. Epub 2022 Jan. 21. PMID: 35061237; PMCID: PMC8850513.

In another clinical study where *Lactobacillus rhamnosus* SP1 was used as a dietary supplement, a 32% reduction in acne lesions was observed and the expression of genes implicated in insulin signaling were normalized. See, Fabbrocini G., Bertona M., Picazo Ó., Pareja-Galeano H., Monfrecola G., Emanuele E. Supplementation with *Lactobacillus rhamnosus* SP1 normalises skin expression of genes implicated in insulin signalling and improves adult acne. Benef. Microbes. 2016; 7:625-630. doi: 10.3920/BM2016.0089.

Moreover, an improvement in the appearance of adult acne in the group taking the dietary supplement was also observed indicating that diets high in the types of carbohydrates that cause rapid increases in blood sugar are involved in acne formation. As was previously mentioned, insulin growth factor 1 (IGF-1) is released in response to a spike in blood sugar levels. Its primary function is to increase glucose uptake by tissues. Unfortunately, IGF-1 also stimulates sebum production, another key factor involved in acne formation. This increase in sebum and its resultant inflammation might represent a link between sugary diets and acne.

Another study investigated whether probiotics taken in combination with minocycline, an antibiotic, would yield an enhanced acne treatment effect and the study was specific to adult women with acne. The study revealed that there was a synergistic anti-inflammatory effect in those taking the combination treatment, and that the probiotics minimized the side effects associated with the antibiotic therapy. See, Jung G W, Tse J E, Guiha I, Rao J. Prospective, randomized, open-label trial comparing the safety, efficacy, and tolerability of an acne treatment regimen with and without a probiotic supplement and minocycline in subjects with mild to moderate acne. J Cutan Med Surg. 2013 March-April; 17(2):114-22. doi: 10.2310/7750.2012.12026. PMID: 23582165. An additional relevant study is J. Clin. Med. 2023, 12(3), 895; https://doi.org/10.3390/jcm12030895.

Several beneficial effects of probiotic consumption have also been demonstrated on other types of dermatological conditions, further reinforcing the existence of the gut-skin axis. For example, skin sensitivity and significant restoration of skin barrier function were reported in individuals after daily oral administration of *Lactobacillus paracasei* (DOI: 10.3920/BM2013.0001).

While the use of conventional topical and oral acne treatments, alone or in combination, provide relief for acne sufferers, there still exists a need for safer and/or more effective treatment options, particularly those involving the use of plant-based actives (botanicals). For example, resveratrol, a natural phytoalexin derived from grapes, is being investigated as one such auxiliary acne treatment option, based on its anti-proliferative, anti-inflammatory, and *C. acnes* inhibiting properties. Its topical use was found to reduce pustular lesions and inflammation, decrease macro- and micro-comedones, and inhibit keratinocyte hyperproliferation. It was also found to inhibit *C. acnes* proliferation on par with benzoyl peroxide and erythromycin.

There is no shortage of other plants and herbs identified in the literature believed to be useful in the treatment of acne. These include topically applied essential oils of *A. millefolium*, bay, benzoin, black cumin, chamomile, *Eucalyptus dives*, geranium, juniper twig, lemon, lemon grass, orange, patchouli, petitgrain, rosemary, safflower oil, sandalwood, sunflower oil, *T. officinale* and thyme. They also list a range of other topical plants/herbs such as: bittersweet nightshade, black walnut, borage, cucumber, duckweed, English walnut, fresh lemon, garlic, grapefruit seeds, oak bark, onion, Oregon grape root, pea, pumpkin, rue, vinegar, vitex and witch hazel. Other ingestible plants/herbs include Brewer's yeast, burdock root, *C. mukul, S. flavescens* and *W. somnifera*. Numerous homeopathic, Indian Ayurvedic therapies and Asian topical therapies were also noted to be used in acne treatment.

While currently available topical and oral acne treatment options have proven to be effective at treating acne, their use oftentimes comes with unpleasant attendant side effects. Topical treatments tend to cause skin irritation, redness, and dryness primarily due to their negative impact on the skin barrier. Oral treatments, while effective at eliminating acne-causing bacterial colonies, tend to cause gut microbiome dysbiosis which negatively impacts skin health by virtue of the body's gut-skin axis. Moreover, oral treatments either focus on just the gut microbiome as a pure probiotic blend, or just the inflammation as an antioxidant blend. The potential synergy of combining an anti-inflammatory asset with a probiotic solution has, to date, not been studied.

As a result, there remains a need for the development of new therapeutic acne treatment assets for treating and managing acne-prone skin with little to no negative side effects that address inherent inflammation and gut dysbiosis, simultaneously.

SUMMARY OF THE INVENTION

According to embodiments, therapeutic compositions and supplements are provided comprising probiotic blends and plant-derived actives, and a method of treating acne-prone skin.

The present disclosure relates to compositions and methods useful for dietary augmentation to provide therapeutic intervention for the treatment and management of acne-prone skin. According to one embodiment of the present disclosure, there is provided an orally administrable composition containing a therapeutically effective amount of: (a) a probiotic blend of bacterial components containing at least: (i) *Lactobacillus acidophilus*, (ii) *Bifidobacterium lactis*, and (iii) *Bacillus coagulans*; (b) guggul; and (c) green tea leaf.

According to another embodiment of the disclosure, the composition contains a therapeutically effective amount of: (a) from about 50 to about 100 mg of a probiotic blend of bacterial components containing at least: (i) *Lactobacillus acidophilus* (e.g., strain 033AE), in an amount of 2 billion colony forming units (CFUs), (ii) *Bifidobacterium lactis* (e.g., strain IDCC 4301), in an amount of 2.4 billion colony forming units (CFUs) and (iii) *Bacillus coagulans* (e.g., strain BC09), in an amount of 2 billion colony forming units (CFUs); (b) from about 500 to about 750 mg of guggul extract; and (c) from about 750 to about 1000 mg of green tea leaf extract, all weights based on the total dry weight of the composition.

In another embodiment, there is provided a method of treating acne-prone skin, comprising orally administering to a human subject in need thereof, a therapeutically effective oral dose of a composition containing: (a) a probiotic blend of bacterial components containing at least: (i) *Lactobacillus acidophilus*, (ii) *Bifidobacterium lactis*, and (iii) *Bacillus coagulans*; (b) guggul; and (c) green tea leaf.

In yet another embodiment, there is provided a method of treating acne-prone skin, comprising orally administering to a human subject in need thereof, a therapeutically effective oral dose of a composition containing: (a) from about 50 to about 100 mg of a probiotic blend of bacterial components containing at least: (i) *Lactobacillus acidophilus* (e.g., strain 033AE), in an amount of 2 billion colony forming units (CFUs), (ii) *Bifidobacterium lactis* (e.g., strain IDCC 4301), in an amount of 2.4 billion colony forming units (CFUs) and (iii) *Bacillus coagulans* (e.g., strain BC09), in an amount of 2 billion colony forming units (CFUs); (b) from about 500 to about 750 mg of guggul extract; and (c) from 750 to about 1000 mg of green tea leaf extract, all weights based on the total dry weight of the composition.

These and other features, aspects and advantages of the present disclosure will become evident to those skilled in the art from a reading of the present disclosure.

DETAILED DESCRIPTION

The compositions of the present invention can comprise, consist essentially of, or consist of, the components of the present invention as well as other ingredients described herein. The term "comprising" as used herein is meant to include various optional, compatible components that can be used in the compositions of the present disclosure. The term "consisting essentially of" as used herein means that the composition or component may include additional ingredients, but only if the additional ingredients do not materially alter the basic and novel characteristics of the compositions or methods.

As used herein, the words "preferred", "preferably" and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not. Further, these numerical ranges should be construed as providing support for a claim directed to any number or subset of numbers within that range.

All percentages, parts, proportions, and ratios as used herein are by weight of the total composition, unless otherwise specified. All such weights as they pertain to listed ingredients are based on the active level.

As used herein, "acne" refers to disorders resulting from the actions of hormones and other substances in the sebaceous glands and hair follicles, which typically lead to clogging of pores and the formation of inflammatory and non-inflammatory skin lesions. Specifically, it refers to blemishes, lesions or pimples, pre-emerging pimples, blackheads and/or whiteheads. As used herein, a "pre-emergent pimple" is an inflamed follicle that is not visually apparent on the surface of the skin to the naked eye (e.g., as a lesion).

The phrase "therapeutically effective amount" as used herein refers to an amount that, when administered to a subject suffering from acne, exhibits an effect of improving, treating, preventing, or inhibiting acne.

As used herein, "treatment" or "treating" means the alleviation, prophylaxis or reversal of a condition, a disease, or a disorder, or at least a discernible symptom thereof. In one embodiment, "treatment" or "treating" refers to a mitigation, prophylaxis, or reversal of at least one measurable physical parameter related to the condition, disease, or disorder being treated, not necessarily discernible in or by the individual, being treated. In yet another embodiment, "treatment" or "treating" refers to inhibiting or slowing the progression of a condition, a disease, or a disorder, either physically, e.g., stabilization of a physiologically discernible symptom, e.g., stabilization of a physical parameter, or both. In yet another embodiment, "treatment" or "treating" refers to delaying the onset of a condition, disease, or disorder.

As used herein, the term 'probiotics' is defined as substances which stimulate the growth of microorganisms, especially those with beneficial properties that give health benefits to the host when orally administered in an appropriate amount. Their established safety and beneficial effects on human health have led to the emergence of probiotics as substitutes or complements to medicines. The advantage of probiotics is that they have very few side effects.

As used herein, the acronym CFU stands for colony forming units.

As used herein, the term "inflammatory skin disorders" refers to skin conditions associated with inflammation including, for example, acne, eczema, psoriasis, and seborrheic dermatitis.

The inventors have surprisingly and unexpectedly discovered that the use of a probiotic-anti-inflammatory dietary supplement compositions in accordance with the present disclosure effectively ameliorate and manage inflammatory skin disorders, especially acne, based on their ability to inhibit gut inflammation associated with general inflammation and follicular inflammation, as well as gut restoring probiotic species that help balance the gut microbiome to further reduce inflammation.

Certain beneficial strains of microbes such as *Lactobacillus*, *Bifidobacterium* and sporulated *Bacillus coagulans* have demonstrated anti-inflammatory and immunomodulatory effects in animals and humans. These strains therefore appear to stimulate quieter immune cells, which could help regulate the immune system throughout the body, including the skin. These three bacteria are included in our acne probiotic, along with ECGC (epigallocatechin gallate), an antioxidant that helps manage intestinal inflammation, and guggul, an Ayurvedic herb containing plant flavonoids and polyphenols (ellagic acid) that are anti-inflammatory and diterpenoids (cambrene, camphorene) that inhibit the inflammatory response.

Accordingly, an object of the present disclosure is to provide compositions for treating acne comprising a therapeutically effective amount of: (a) a probiotic blend of bacterial components containing at least: (i) *Lactobacillus acidophilus*, (ii) *Bifidobacterium lactis*, and (iii) *Bacillus coagulans*; and (b) guggul; and (c) green tea leaf, wherein the composition is administered orally.

Another object of the present invention is to provide a method of treating and managing acne-prone skin comprising orally administering to a person in need thereof a therapeutically effective amount of a composition containing: (a) a probiotic blend of bacterial components containing at least: (i) *Lactobacillus acidophilus* 033AE, (ii) *Bifidobacterium lactis* IDCC 4301, and (iii) *Bacillus coagulans* BC09; and (b) guggul extract; and (c) green tea leaf extract.

The *Lactobacillus acidophilus* bacterium of the present invention is a beneficial bacterium commonly used as a probiotic. It is naturally found in the body, as well as in fermented foods such as sauerkraut and helps to support both the immune and digestive systems, as well as to inhibit endoplasmic reticulum stress. It may be employed in the form of live cells or fermentation products (supernatants).

In some embodiments, the *Lactobacillus acidophilus* bacterium is employed in an amount of from about 1 to about 20 billion CFU, such as from about 1 to about 10 billion CFU, and particularly about 2 billion CFU.

The *Bifidobacterium lactis* of the present invention has been found to reduce inflammatory and T cells mediators and to promote regulatory T cells specific markers; specifically, a trend toward a diminution of mucosal thickness and attenuated epithelial damage was revealed when it was administered as a probiotic. The *Bifidobacterium* genus is in general also seen as anti-inflammatory.

In some embodiments, the *Bifidobacterium lactis* bacterium is isolated from the feces of breastfed infants and is employed in an amount of from about 1 to about 20 billion colony forming units CFU, such as from about 1 to about 10 billion CFU, and particularly about 2.4 billion CFU.

The *Bacillus coagulans* is a non-pathogenic, Gram positive, spore-forming bacterium that produces L (+) lactic acid (dextrorotatory) under homo-fermentation conditions. It has been isolated from natural sources, such as heat-treated soil samples inoculated into nutrient medium (see e.g., Bergey's Manual of Systemic Bacteriology, Vol. 2, Sneath, P. H. A. et al., eds., Williams & Wilkins, Baltimore, Md., 1986). *Bacillus coagulans* has also been utilized to produce lactic acid (U.S. Pat. No. 5,079,164). Though not naturally found in the gut, *Bacillus coagulans* strains have been used as general nutritional supplements and agents to control constipation and diarrhea in humans and other animals.

In some embodiments, the *Bacillus coagulans* is employed in an amount of from about 1 to about 20 billion colony forming units CFU, such as from about 1 to about 10 billion CFU, and particularly about 2 billion CFU.

Both the *Lactobacillus acidophilus* and *Bifidobacterium lactis* may be employed in the form of live cells or dead cells, respectively, whereas the *Bacillus coagulans* is employed in spore-based form to ensure survival in stomach acid and bioavailability in the body's large intestine.

In some embodiments, the probiotic blend is employed in a therapeutically effective amount which can include from about 50 to about 100 mg, including from about 75 to about 80 mg, and particularly about 77 mg, all weights based on the total dry weight of the composition.

The composition of the present disclosure further includes plant-derived components used as ancillary acne treating agents. Guggul is derived from the guggul plant, *Commiphora mukul* and has both anti-inflammatory and antioxidant properties that protect the body from oxidative stress. The guggul is employed in a therapeutically effective amount which can include from about 500 to about 750 mg, including from about 500 to about 600 mg, and particularly about 525 mg, all weights based on the total dry actives of the composition.

The active compounds found in guggul include gugulipid and guggulsterone. In some embodiments, the guggul used in the present disclosure is employed in a therapeutically effective amount which can include from about 25 to about 75 mg, including from about 45 to about 60 mg, and particularly about 50 mg of guggulsterone, all weights based on the total dry weight of the composition.

Another plant-derived component employed as an ancillary acne treating agent in the present disclosure is green tea leaf which has been shown to help keep skin healthy due to its anti-inflammatory properties. Its primary active compound, epigallocatechin-3-gallate (EGCG) has been shown to promote anti-inflammatory responses when applied topically onto the skin. In some embodiments, the green tea leaf is employed in a therapeutically effective amount which can include from about 750 to about 1000 mg, including from about 800 to about 900 mg, and particularly about 840 mg, all weights based on the total dry actives of the composition. The amount of EGCG employed is well below, by a factor of 2, the toxicity limit associated with the use of this ingredient.

In some embodiments, the green tea leaf used in the present disclosure is employed in a therapeutically effective amount which can include from about 200 to about 500 mg, including from about 300 to about 400 mg, and particularly about 360 mg of EGCG, all weights based on the total dry weight of the composition.

According to one embodiment of the present disclosure, there is provided a composition for treating acne comprising a therapeutically effective amount of: (a) a probiotic blend of bacterial components containing at least: (i) from about 1 to about 20 billion CFU of *Lactobacillus acidophilus*, (ii) from about 1 to about 20 billion CFU of *Bifidobacterium lactis*, and (iii) from about 1 to about 20 billion CFU of *Bacillus coagulans*; and (b) from about 500 to about 750 mg of guggul containing from about 25 to about 75 mg guggulsterone; and (c) from about 750 to about 1000 mg of green tea leaf containing from about 200 to about 500 mg of EGCG, all weights based on the total dry weight of the composition, and wherein the composition is administered orally.

According to yet another embodiment of the present disclosure, there is provided a composition for treating acne comprising a therapeutically effective amount of: (a) a probiotic blend of bacterial components containing at least: (i) from about 1 to about 10 billion CFU of *Lactobacillus acidophilus*, (ii) from about 1 to about 10 billion CFU of *Bifidobacterium lactis*, and (iii) from about 1 to about 10 billion CFU of *Bacillus coagulans*; and (b) from about 500 to about 600 mg of guggul containing from about 45 to about 60 mg of guggulsterone; and (c) from about 800 to about 900 mg of green tea leaf containing from about 300 to about 400 mg of EGCG, all weights based on the total dry weight of the composition, and wherein the composition is administered orally.

According to a particular embodiment of the present disclosure, the composition contains a therapeutically effective amount of: (a) a probiotic blend of bacterial components containing at least: (i) *Lactobacillus acidophilus*, in an amount of about 2 billion CFU, (ii) *Bifidobacterium lactis*, in an amount of about 2.4 billion CFU and (iii) *Bacillus coagulans*, in an amount of about 2 billion CFU; and (b) a mixture of plant-derived s comprising at least: (1) about 525 mg of guggul containing about 50 mg of guggulsterone; and (2) about 840 mg of green tea leaf containing about 360 mg of EGCG, all weights based on the total dry weight of the composition.

According to an embodiment of the present disclosure, the composition contains a therapeutically effective amount of: (a) about 77 mg of a probiotic blend of bacterial components containing at least: (i) *Lactobacillus acidophilus* (e.g., strain 033AE), in an amount of 2 billion colony forming units (CFUs), (ii) *Bifidobacterium lactis* (e.g., strain IDCC 4301), in an amount of 2.4 billion colony forming units (CFUs) and (iii) *Bacillus coagulans* (e.g., strain BC09), in an amount of 2 billion colony forming units (CFUs); and (b) a mixture of plant-derived extracts comprising at least: (1) about 525 mg of guggul extract containing about 50 mg of guggulsterone; and (2) about 840 mg of green tea leaf extract containing about 360 mg of EGCG, all weights based on the total dry weight of the composition.

Since the compositions of the present disclosure are meant to be orally administered, the use of a carrier suitable for ingestion should be used. If the composition is employed in dry form, such as in the case of an enterically coated capsule, the formulation agents and excipients used to make the capsules are well known in the field. The rationale behind the use of compositions in an encapsulated form is to significantly improve their survival time as they travel through the body. In such a case, the use of certain types of capsules can retard or prevent the degradation of the microorganism in the gastrointestinal tract. It should be noted, however, that the compositions may be employed in any type of galenic form typically used for oral administration.

Besides their direct and independent benefits, the ingredients of the dietary supplements of this invention are believed to work together synergistically in a manner that powerfully enhances each ingredient's level of efficacy, thereby further promoting their beneficial acne treatment effect. Without intending to be bound by theory, the inventors believe that the combination of: (1) the disclosed probiotic blend and its ability to positively impact acne-prone skin by enhancing gut microbiome symbiosis which leads to improved skin health via the gut-skin axis; (2) the metabolism enhancing/anti-inflammatory/antioxidant properties of guggul; and (3) powerful anti-inflammatory effects of green tea leaf, results in a synergistic decrease in inflammation and acne-causing bacterial colonies in acne-prone skin.

According to yet another embodiment, the present disclosure is also directed to a method of treating acne-prone skin, comprising orally administering to a human subject in need thereof, a therapeutically effective oral dose of the above-disclosed compositions.

In another embodiment, the method can further include topically applying a therapeutically effective amount of an ancillary treatment composition containing at least one active ingredient chosen from benzoyl peroxide, adapalene, sulfur, salicylic acid, azelaic acid, alpha hydroxy acids, bakuchiol, retinol, retinoids, glycolic acid, tretinoin, erythromycin and clindamycin.

EXAMPLES

Acne is a chronic inflammatory condition that is estimated to affect more than 85% of the population at some point. While antibiotics are typically used for systemic therapy, they can increase a person's risk for developing drug-resistance to bacteria while shifting the gut microbiome in a negative direction.

The following examples as set forth herein are intended for illustrative purposes only and are not intended to limit the scope of the disclosure in any way, as many variations thereof are possible without departing from the spirit and scope of the disclosure. In the example, all concentrations are listed as dry weight percent, unless otherwise specified.

Example 1

| Ingredient | % dry wt/wt (mg) | % actives |
|---|---|---|
| Probiotic blend | 77 | |
| L. acidophilus | | 2 billion CFUs |
| Bifidobacterium lactis | | 2.4 billion CFUs |
| Bacillus coagulans | | 2 billion CFUs |
| Guggul | 525 | 50 mg guggulsterone |
| Green tea leaf | 840 | 360 mg EGCG |

The composition of Example 1, in capsule form, was evaluated to assess its impact on individuals suffering from acne. A clinical study was performed on a group of chronic acne sufferers, aged 12 to 45, to determine what, if any, benefit could be realized by taking the supplement of Example 1. Each participant was asked to take a daily dose of the composition of Example 1 over a period of 8 weeks. The participants were classified as having mild to moderate acne, based on the investigator's global assessment, and had to have at least 10 inflammatory lesions, and at least 5 non-inflammatory lesions to qualify for the study. The main testing method for judging efficacy was inflammatory (papules and pustules) and non-inflammatory (open and closed comedones) lesion counting. The results of the study are found in Table 1 below.

TABLE 1

| | Non-inflammatory lesion change from baseline (%) | | Inflammatory lesion change from baseline (%) | |
|---|---|---|---|---|
| | Week 4 | Week 8 | Week 4 | Week 8 |
| Average Improvement | −29.50% | −48.10% | −47.4 | −57.3 |
| SEM | 5.70% | 6.40% | 5.70% | 6.20% |
| p Value | 0.0001202 | 0.0000029 | 0.0000005 | 0.0000002 |

As can be seen from the results in Table 1, chronic acne sufferers realized both a statistically and clinically significant reduction in both inflammatory lesions (papules and pustules) and non-inflammatory lesions (open and closed comedones).

What is claimed is:

1. An orally administrable dietary supplement composition comprising a therapeutically effective amount of: (a) a probiotic blend of bacterial components containing at least: (i) from about 1 to about 20 billion CFU of *Lactobacillus acidophilus*, (ii) from about 1 to about 20 billion CFU of *Bifidobacterium lactis*, and (iii) from about 1 to about 20 billion CFU of *Bacillus coagulans*; and (b) from about 500 to about 750 mg of guggul containing from about 25 to about 75 mg guggulsterone; and (c) from about 750 to about 1000 mg of green tea leaf containing from about 200 to about 500 mg of epigallocatechin-3-gallate (EGCG), wherein all weights are based on the total dry weight of the composition.

2. The composition of claim 1, wherein (a) comprises: (i) from about 1 to about 10 billion CFU of *Lactobacillus acidophilus*, (ii) from about 1 to about 10 billion CFU of *Bifidobacterium lactis*, and (iii) from about 1 to about 10 billion CFU of *Bacillus coagulans*; wherein (b) comprises from about 500 to about 600 mg of guggul containing from about 45 to about 60 mg of guggulsterone; and wherein (c) comprises from about 800 to about 900 mg of green tea leaf containing from about 300 to about 400 mg of EGCG, all weights based on the total dry weight of the composition.

3. The composition of claim 1, wherein (a) comprises: (i) *Lactobacillus acidophilus*, in an amount of about 2 billion CFU, (ii) *Bifidobacterium lactis*, in an amount of about 2.4 billion CFU and (iii) *Bacillus coagulans*, in an amount of about 2 billion CFU; wherein (b) comprises about 525 mg of guggul containing about 50 mg of guggulsterone; and wherein (c) comprises about 840 mg of green tea leaf containing about 360 mg of EGCG, all weights based on the total dry weight of the composition.

4. A method of treating acne-prone skin comprising orally administering the composition of claim 1 to a human subject in need thereof.

5. A method of treating acne-prone skin comprising orally administering the composition of claim 2 to a human subject in need thereof.

6. A method of treating acne-prone skin comprising orally administering the composition of claim 3 to a human subject in need thereof.

7. The method of claim 4, wherein the composition is orally administered on a daily basis.

8. The method of claim 7, wherein the composition is orally administered over a period of about 8 weeks.

9. The method of claim 4, further comprising topically applying a therapeutically effective amount of an ancillary treatment composition containing at least one active ingredient selected from benzoyl peroxide, adapalene, sulfur, salicylic acid, azelaic acid, alpha hydroxy acids, bakuchiol, retinol, retinoids, glycolic acid, tretinoin, erythromycin, clindamycin, or combinations thereof.

10. The method of claim 5, further comprising topically applying a therapeutically effective amount of an ancillary treatment composition containing at least one active ingredient selected from benzoyl peroxide, adapalene, sulfur, salicylic acid, azelaic acid, alpha hydroxy acids, bakuchiol, retinol, retinoids, glycolic acid, tretinoin, erythromycin, clindamycin, or combinations thereof.

11. The method of claim 6, further comprising topically applying a therapeutically effective amount of an ancillary treatment composition containing at least one active ingredient selected from benzoyl peroxide, adapalene, sulfur, salicylic acid, azelaic acid, alpha hydroxy acids, bakuchiol, retinol, retinoids, glycolic acid, tretinoin, erythromycin, clindamycin, or combinations thereof.

12. The method of claim 5, wherein the composition is orally administered on a daily basis.

13. The method of claim 12, wherein the composition is orally administered over a period of about 8 weeks.

14. The method of claim 6, wherein the composition is orally administered on a daily basis.

15. The method of claim 14, wherein the composition is orally administered over a period of about 8 weeks.

* * * * *